US007785467B2

(12) United States Patent  (10) Patent No.: US 7,785,467 B2
Logan et al.  (45) Date of Patent: Aug. 31, 2010

(54) METHOD, COMPOSITION AND APPARATUS FOR HIGH TEMPERATURE PRODUCTION OF METHANE FROM POULTRY WASTE

(75) Inventors: John William Logan, Prentiss, MS (US); Sumesh Mohan Arora, Madison, MS (US); Bill Henry Johnson, Prentiss, MS (US); Richard L Vetter, Elgin, IL (US); Clarence Monte Howard, Pinola, MS (US)

(73) Assignee: Eagle Green Energy, LLC, Prentiss, MS (US)

( * ) Notice: Subject to any disclaimer, the term of this patent is extended or adjusted under 35 U.S.C. 154(b) by 649 days.

(21) Appl. No.: 11/803,599

(22) Filed: May 15, 2007

(65) Prior Publication Data

US 2008/0283468 A1 Nov. 20, 2008

(51) Int. Cl.
*C02F 3/28* (2006.01)
(52) U.S. Cl. .............. 210/603; 210/612; 210/175; 210/194
(58) Field of Classification Search ............ 210/603, 210/612, 613, 631, 175, 188, 194, 252, 259, 210/903, 908; 71/10, 21; 435/262, 262.5
See application file for complete search history.

(56) References Cited

U.S. PATENT DOCUMENTS

| | | | |
|---|---|---|---|
| 4,482,458 A * | 11/1984 | Rovel et al. ............... | 210/603 |
| 5,096,579 A | 3/1992 | Jordan | |
| 5,411,567 A | 5/1995 | Ueotani | |
| 5,705,057 A * | 1/1998 | Hoffa ..................... | 210/150 |
| 5,942,116 A * | 8/1999 | Clark et al. .............. | 210/603 |
| 6,254,775 B1 | 7/2001 | McElvaney | |
| 6,299,774 B1 * | 10/2001 | Ainsworth et al. ......... | 210/603 |
| 6,521,129 B1 | 2/2003 | Stamper | |
| 6,569,332 B2 * | 5/2003 | Ainsworth et al. ......... | 210/603 |
| 2002/0192809 A1 * | 12/2002 | Lanting et al. ........... | 435/290.1 |
| 2003/0057152 A1 * | 3/2003 | Haridas ................... | 210/603 |

\* cited by examiner

*Primary Examiner*—Fred Prince
(74) *Attorney, Agent, or Firm*—Terry B. Morris

(57) ABSTRACT

Compositions, methods and apparatus for the production of methane gas from poultry litter are provided. Particular features are selection of methanogens, well stirring of the digester, and control of critical parameters of digester temperature, pH, and solids content resulting in enhanced methane production and reduced nitrogen compositions. A benefit of the invention is the capability to maintain a closed system without waste by-products.

25 Claims, 5 Drawing Sheets

METHOD, COMPOSITION AND APPARATUS FOR HIGH TEMPERATURE PRODUCTION OF METHANE FROM POULTRY WASTE

CROSS REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of the Invention

The present invention relates generally to bioconversion of animal waste to useful products, and more particularly, but not by way of limitation, to methods of treating poultry manure using thermophilic anaerobic digestion.

2. Brief Description of the Art

The present invention is directed to methods for treating manure which involve anaerobic digestion. Conventional anaerobic digestion technology has certain limitations in terms of reaction rates and the ability of the bacteria to be productive when conditions (such as pH, temperature and concentration of certain chemical constituents) in the digester are not optimum. The anaerobic digestion process depends on a collection of bacteria collectively known as anaerobes, and such bacteria systematically break down organic material into simple molecules.

The conversion of animal waste into useful products such as methane and fertilizers using anaerobic digestion is a well established technique in theory and practice. Numerous farms in the United States and around the world are now successfully capturing methane gas that is released from either an anaerobic digester or a covered lagoon. The gas produced is generally utilized to generate electricity or combusted to provide heat for local operations. The majority of such projects are located on swine or dairy operations. Some efforts have been made to adopt such conversions to poultry operations, with most such efforts directed to egg laying poultry and virtually none to broiler operations.

One example of such effort for egg-laying poultry operations is found in U.S. Pat. No. 6,521,129 B1 ("U.S. Pat. No. 6,521,129"), the entirety of which is incorporated herein by reference. In U.S. Pat. No. 6,521,129 the prior art methodology of dilution of the difficult to treat poultry manure was recognized, as well as the potentially inhibitory parameters of digester temperature, oxygen or air intrusion, pH fluctuation, and build up of toxic constituents such as ammonia, hydrogen sulfide or excess volatile fatty acids. The solution in U.S. Pat. No. 6,521,129 was to add raw material to a mixing vessel containing a digester liquid which has been largely depleted of digestible organic materials but containing a similar mineral content as the raw manure, subsequently filtering to remove solids to produce a liquid containing ammonia and reactive organic materials, heating to an elevated range to produce ammonia and kill bacteria, removing the ammonia, cooling the remaining liquid to a digestion temperature. One feature of U.S. Pat. No. 6,521,129 is the control of the ammonia concentration to maintain it below inhibitory levels.

Those in the art recognize that such different operations produce differing waste materials as potential feed material to generate methane. The handling, storage and disposal of poultry litter is becoming more regulated and, resultantly, a financial and management burden to the poultry farmer. What is needed is a method of poultry waste management which addresses such concerns.

DETAILED DESCRIPTION OF THE PREFERRED EMBODIMENT

Figure 1:
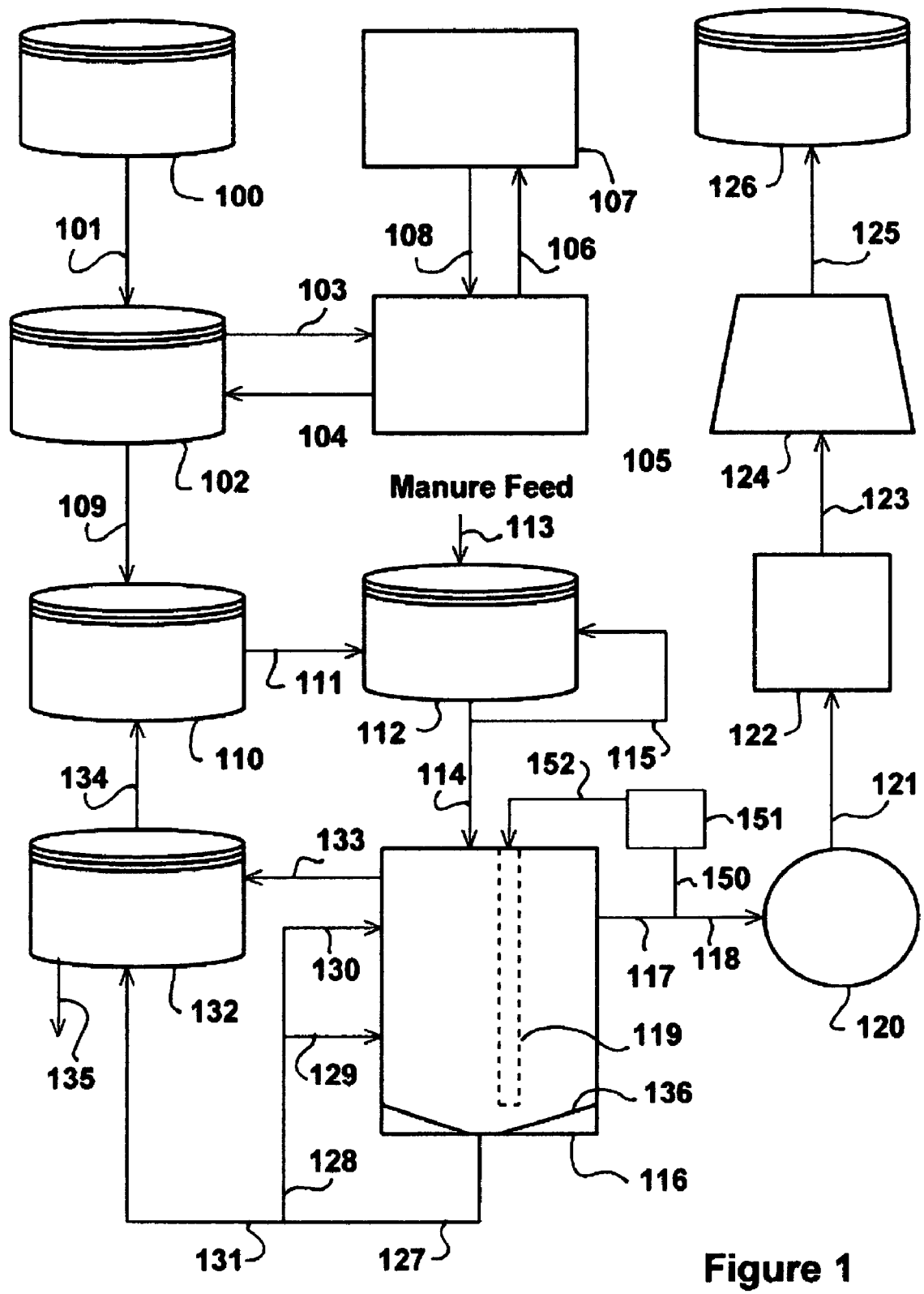
FIG. 1 is a flow diagram of one embodiment of the present invention.

Briefly, the present invention includes adding raw manure to a mixing vessel containing a digester liquid which has microbial agent suitable for digesting the waste to produce methane gas and to enable the recovery of nitrous and other compounds for use.

An important feature of the present invention is the production in the digester of a composition comprising an admixture of a poultry litter derivative, one or more members of a thermophilic methanogenic genera, each of said member capable of growing by acetoclastic reaction, and water. The poultry litter derivative, the one or more members of methanogens and water are admixed in an effective ratio to produce methane, which becomes a part of the admixture, as well as additional components from the digestion process.

The poultry litter derivative is recovered waste manure from a poultry operation. While it is typical on poultry farms that waste recovered from poultry houses contains a significant amount of cellulosic material used as floor covering and other uses, the operation producing the derived waste useable in the present invention has been controlled so as to substantially reduce, if not essentially eliminate, the amount of cellulosic material. Preferably, the derivative composition contains less than about 5 weight percent cellulosic material. The poultry litter derivative may also contain a portion of water, but there is no critical amount of water which need be present during its handling and transportation to the mixing tank hereinafter discussed. Although the preferred "poultry litter derivative" is described here, manure without beneficiation can be used though cellulose content can be problematic.

A preferred method of controlling the content of such waste manure contents is to skim the waste from the poultry house floor, taking only a clean portion of the waste, e.g. with reduced or no cellulose content, The remaining portion is then turned, back-mixed or similarly handled in preparation for use with continuing operations to serve as a base for receipt of additional operational waste and to foster cellulose degradation.

Further, the preferred waste is litter derived from broiler chicken production operations. The typical feed material for broiler operations produces the preferred litter waste for use in the present invention. A particular concern is to ensure that nitrogen content in the waste is maintained as low as production needs can allow.

The poultry litter derivative comprises an amount of solids which enables a balancing of the methanogens and acids in the digester; it being understood that the critical growth of the methanogens must out-compete the formation of acids, such as acetic acids and other organic acids. The effective percentage of solids is accordingly that amount which enables the balancing of methanogen growth and acid production in accordance with the objective of the present invention. Accordingly, the amount of solids and liquids, such as water, in the poultry litter derivative feed stream and the amount of solids and liquids in any recycled portion, are preferably admixed with the digester contents to produce about 1% to about 10% solids by volume of the digester liquid composition, more preferably about 5% to about 6% solids by volume. Water is preferably used as a mixing medium liquid, preferably hot, more preferably about 180 degrees Fahrenheit. One method of measuring solids content is the viscosity of the digester liquid phase, typically performed as a pre-mix to the product and recycle lines. This can be conveniently performed in the associated storage facilities.

The preferred one or more member(s) of a thermophilic methanogenic genera is selected from the group consisting of the genus *Methanosarcina* and the genus *Methanosaeta*. More preferred is a *Methanosarcina barkeri*, even more preferably the member is *Methanosarcina barkeri* fusaro. As will be appreciated by the artisan, these bacteria can evolve through selection in response to the environmental conditions over time in the digester, becoming specialized or even evolving into new species.

The composition in the anaerobic digester is kept at a pH level suitable for the methane production from the waste by the thermophilic methanogenic agent. Preferably, the pH of the composition is at least about 7.0 and no more than the maximum pH to produce methane from said composition for the particular constituents in the digester tank. More preferably, the pH is between 7.0 and about 7.5. At least in part, the control of the pH may be done by the control of feed to the digester.

The composition in the anaerobic digester is kept at a temperature level suitable for the methane production from the waste by the thermophilic methanogenic agent. The preferred temperature is one which kills pathogens which may be present in the composition as well as a temperature that is beneficial in the production of methane gas. Preferably, the temperature of the composition is at least about 120 degrees and no more than the maximum temperature effective to produce methane from said composition. More preferably, the temperature of the composition is between about 120 degrees and about 150 degrees, even more preferably higher than about 135 degrees. All references herein to degrees of temperature are in terms of degrees Fahrenheit.

The operation of the digester takes into consideration coordination of the temperature and pH levels of the digesting slurry mass. The sensing of these parameters may be by direct collection and analysis of samples and/or by the use of strategically positioned sensing probes for collecting data for computerized analysis. A consideration is that as either the pH or the temperature of the slurry increases, the unwanted generation of ammonia may increase. For example, an increase in pH may require the lowering of temperature to maintain the desired methanogen production, or vice versa. A third control parameter can also be the mass feed rate of the poultry litter derivative, particularly as such affects the concentration of solids in the digester. Make-up water may be required as well and should be considered a component of this parameter. Preferably, the feed rate of waste into the digester, the digester temperature, and the pH of the digester are effectively controlled to produce the desired methanogen production, methane production and ammonia production.

The digester composition is agitated to produce a reaction mixture of gaseous product, e.g. primarily methane, and a pumpable slurry. The pumpable slurry preferably is well mixed toward a state of homogeneity such that the digester methanogens and the suspended solids interact so that the suspended solids can act as a substrate for the methanogens. Well mixing of the digester liquid phase is also important in accurately sensing the reaction parameters to control the digester process.

One embodiment of the present invention is an apparatus useful for practicing the methods of the invention. The apparatus is a vessel suitable for containing anaerobic digestion materials. This vessel can be a production tank constructed of materials suitable for containing the animal waste and biological agent(s) suitable for converting said waste into gaseous and liquidous products, as discussed herein.

The apparatus contains mixing means for mixing said anaerobic digestion materials. The feature of the mixing means is to produce the well mixing discussed above to achieve as much methanogen-substrate interaction. Another feature is to provide as much suspension of solids in the digester, it being a tendency of solids to settle in the bottom of the digester. Another feature of the mixing means is to reduce or prevent the formation of crust on the surface of the liquid portion of the digester contents. Yet another feature is the attaining of substantial, if not complete, homogeneity conditions in the digester to enable suitable sensing of parameters and resulting control of the digester process.

While mechanical stirring equipment, such as agitators for example, can be used, the preferred mixing means is a first fluid injection means for imparting annular flow momentum in the materials in the vessel and a second fluid injection means for imparting axial flow momentum in the materials in the vessel. The means can be present in one physical structure or contain in separate devices. The operation of the mixing means can be continuous, intermittent and/or independent of each other.

For instance, a preferred device as a mixing means for imparting annular flow is a first, inner tube extending concentrically inside a second, outer tube. This second tube is entirely within the digester tank and vertically suspended, such as by struts or cross bars. The upper end of this second tube opens below the interior gas-containing headspace region of the digester tank. The lower end extends towards the bottom of the digester tank and opens into the slurry mass portion of the digester tank. Preferably, this lower end opens in the proximity of settled solids in the bottom of the digester tank. The axis of these concentrically aligned tubes is preferably near or at the central axis of the digester tank.

The first tube communicates with a source outside the digester. Preferably this tube is the terminus of a recycle line drawing from a product line of the digester or from the digester itself. The terminal opening in the first tube permits the injection of fluid from the first tube into the second tube. Preferably, the fluid is recycled methane extracted from the digester tank, but can be other fluids, such as process liquids or make-up water as non-limiting examples. The positioning of the first tube's terminal opening and the injection of fluid material effectively results in an upward flow of material inside the second, outer tube, that is the annular space between the two tubes concentrically aligned, that is, between the outer surface of the first tube and the inner surface of the second tube. This is achieved by the proper configuring of the injection means, such as a nozzle, to permit the natural upward rise of gas or to direct gas or liquid flow up this annular space inside of the second tube. This upward flow preferably produces sufficient slurry mass draw into the lower end of the second tube to entrain at least some, preferably all, of any settled solids at the bottom of the digester tank. In a preferred configuration of the tank, the bottom of the tank is conically shaped with the point downward to act to collect settling solids near the central axis of the tank.

The slurry and injected fluid liquid (e.g. gas) masses inside the annular space are expelled at the top and broadcasted through the upper region of the digester's liquid phase, enabling suspension of the entrained solids in the slurry mass. This activity into the upper portion of the slurry mass is preferably sufficient to reduce or eliminate the formation of crust on the slurry surface. Most, if not all, of any entrained gas in the upward flowing mass admixes with the gas in the headspace region and is ultimately withdrawn as production gas. As slurry mass is removed from the bottom of the digester tank and expelled inside the top of the digester tank, an overall annular circulation flow pattern results with a downward flow of slurry mass between the digester tank inner wall and the second tube outer wall.

At a separate time or simultaneously, an axial flow momentum of slurry mass between the digester tank inner wall and the second tube outer wall about the digester tank vertical axis can be created by gas or fluid injection of material. Preferably, this can be accomplished by injecting feed material or by recycling product mass extracted from the digester tank, which material is then injected at a tangential angle to the tank's central vertical axis to impart circulation about the vertical axis. As a non-limiting example, nozzles to introduce material can be configured with an angle of about 30 degrees from the tangent to the digester tank wall. These injection nozzles can be placed conveniently at a single or multiple level in the slurry mass inside the digester tank. The injected mass imparts a momentum in the slurry to cause circulation about the vertical axis of the digester tank. Control of these flows, as with the other flows discussed herein, can be conveniently monitored and controlled by computerized processing.

The separate two flow patterns or the resultant flow pattern of the two mixing means can be coordinated, preferably via computers, to produce the desired mixing patterns of the digester.

The apparatus contains a temperature control means for heating the anaerobic digestion materials to the desired temperature. A preferred means is a set of heating tubes internal to the vessel for heat exchange with the digester materials. The heat exchange values can be conveniently obtained from external heat sources. The preferred internal location is near the internal walls and relatively low in the tank.

The apparatus will have at least one feed line suitable for feeding said animal waste into the vessel, and at least one gaseous product line for extracting gaseous product from the vessel, and at least one liquidous product line for extracting a liquid product from said vessel. Other lines, such as make up fluid lines as an example, can be used if preferred. Preferably, the vessel has a sloped bottom suitable for guiding the liquid product into the liquidous product line. A suitable coating of the sloped bottom floor is preferred to prevent adhering or other obstructive behavior of the material flow in the vessel. A preferred coating material is an epoxy to prevent buildup of the reaction mass.

Appropriate sensor of the reaction parameters of concern can be conveniently positioned throughout the system. By appropriate location and programming strategy, the well mixed digester enables control of the production process.

Referring to FIG. 1, there is depicted a flow diagram of one embodiment of the present invention. Process water is stored in water tank 100 and fed through line 101 to heating tank 102. Water is cycled through line 103 to heat exchanger unit 105 and returned to heating tank 102 through line 104. A heating fluid is cycled through line 106 to solar panel unit 107 and returned to heat exchanger unit 105 in line 108. While heat is captured in this example from the solar panel unit 107, it is to be understood that there are opportunities from process flows in the system as a whole from which heat can be captured in the heat exchanger unit 105 or heating tank 102 and not wasted into the ambient environment. Heated process water exits through line 109 and enters into water tank 110. As process requirements are made, the heated process water flows through line 111 into mixing tank 112. Also fed into mixing tank 112 is process ready chicken manure flowing through manure feed line 113. This may be achieved, as a non-limiting example, by simply manually dumping the waste into tank 112. Appropriate mixing means are employed in mixing tank 112 to achieve a desired mixing product ready for introduction via mixed product line 114 into digester tank 116. A desired amount of mixed product is recycled through recycle line 115 back into the mixing tank 112. A preferred result of recycling through line 115 is to enable continuous mixing of the slurry in tank 112 prior to it being fed into tank 116. In a preferred embodiment, in addition to recycle line 115, or in place of line 115, the manure feed in line 113 is premixed with a recycled portion of the contents of tank 112 prior to its introduction into tank 112. The gaseous product produced in digester tank 116 is withdrawn through gas product line 117. A portion of this gaseous product is fed via line 118 into chiller system 120 and a separate portion of this gaseous product is recycled through gas recycle line 150 through pump 151 and feed under pressure via line 152 into tube 119. In a preferred option of the configuration of the present apparatus to recycle gas through gas recycle line 152, a storage tank (not shown in the drawings) is positioned as a part of gas recycle line 152 between pump 151 and tube 119 and has storage and control means to enable the build-up of pressure in the storage tank until a pre-determined pressure has been achieved, then via the control means permitting the sudden release of gas into tube 119, thereby creating a controlled burst of gas into tube 119, forceably lifting the solution and entrained solids therein from the tube 119. In yet in another preferred embodiment, either in place of or in addition to the recycling of gaseous product through line 150, a take-off line (not depicted in the Figures herein) is used to recycle a portion or all of the gaseous product from line 125 exiting the compressor 124, which operation is described hereinafter. In either case, the gaseous product reintroduced into digester tank 116 is used in the reaction process as discussed below. The gaseous product from chiller system 120 flows through chiller product line 121 into scrubber system 122. The desired gaseous product then flows from scrubber system 122 through scrubber product line 123 into compressor 124, where it is compressed to a desired pressure. The compressed product then exits the compressor 124 through compressed product line 125, flowing into gas storage tank 126. A second product stream exits digester tank 116 through liquid product line 127. A portion of the product recycles through recycle line 128, which splits into lower recycle feed line 129 and upper recycle feed line 130 before reentering digester tank 116. The non-recycled portion of the products flows through liquid product line 131 into product storage tank 132. Also present is overflow line 133, which enables in part the fluid level control in digester tank 116. Liquid product exits storage tank 132 through line 134 for part of an overall recycle flow through water tank 110. A separate product cut exits storage tank 132 via line 135. A feature of the digester tank 116 is noted in the presence of sloped bottom 136. This sloped floor assists in the well-mixing of the reactants in the digester and assists in directing material into line 127. Also a feature which contributes is the preferred mechanical configuration of the injection ports of the recycled product reentering the digester through lines 129 and 130. Preferably, the lines are configured to produce an axial flow of reactant material in the tank. This is combined with the preferred use of the tube 119 which can be configured to produce an annular, circular flow induced by the upward flow of gas.

Figure 2:
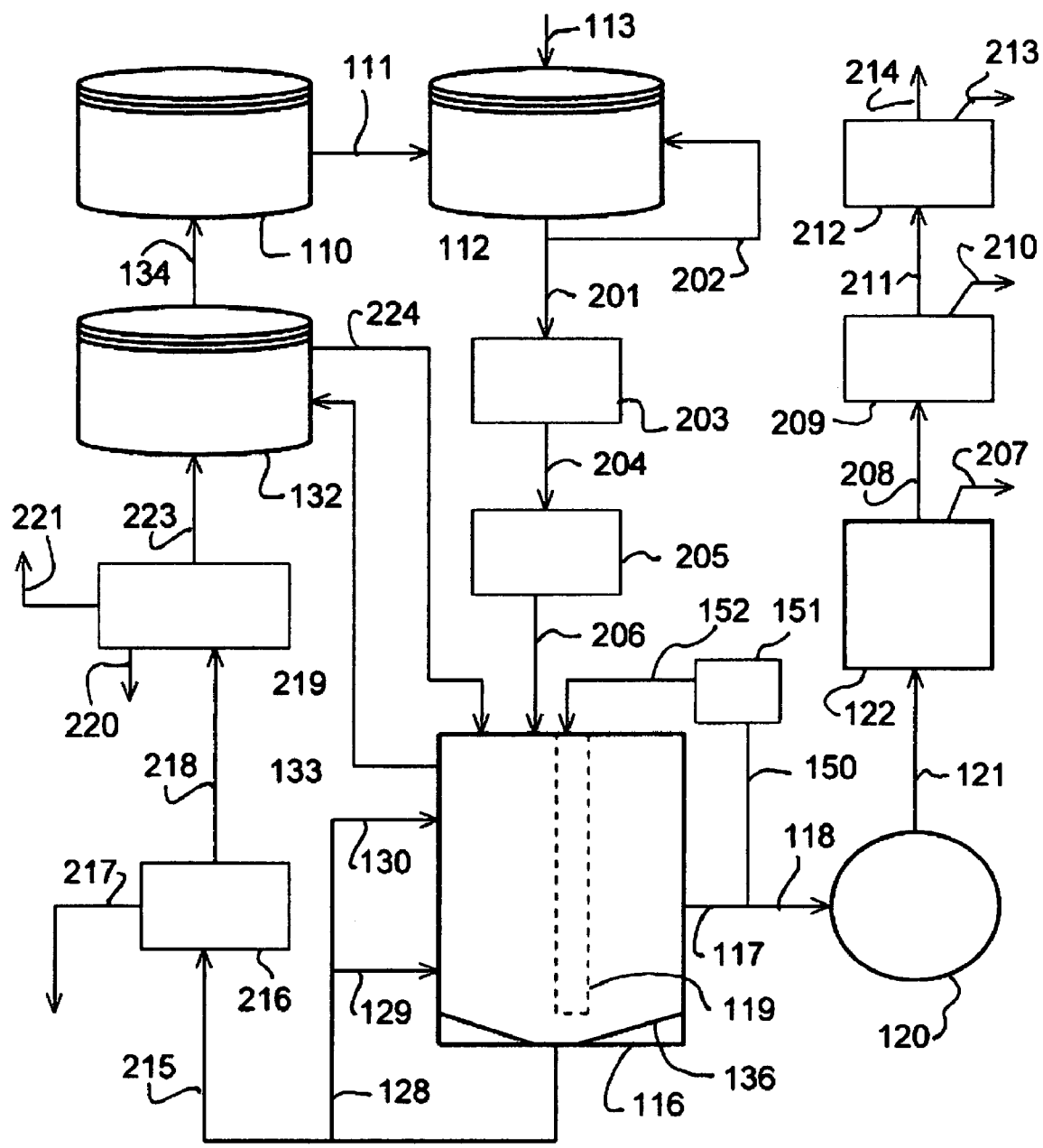
FIG. 2 is a flow diagram of additional features of a similar embodiment of the present invention.

Referring to FIG. 2, there is depicted a portion of a system similar to that in FIG. 1, which has been modified. The portion of the system in FIG. 1 containing the equipment before the feed through line 109 is omitted for brevity and to permit focus on the additional features in FIG. 2. There is water tank 110 from which heated process water flows through line 111 into mixing tank 112. Prepared feed flows through manure feed line 113. Product is extracted through mixing product line 201 with a portion recycled through recycle line 202 into mixing tank 112. The other portion of product flows into screen 203 from which screened mixing product continues through screen product line 204 into preheater 205. The heated mixing product then flows through preheater product line 206 into digester tank 116. Similar to the previous figure, gaseous product is extracted through gas product line 117 with a portion recycled via gas recycle line 150. Another portion of the gaseous product flows into chiller system 120. The extracted chilled product is sent via chiller product line 121 into scrubber system 122 for treatment. Unwanted hydrogen sulfide gas exits via hydrogen sulfide product line 207 and the scrubbed product is then sent via scrubber product line 208 into water filter 209 for removal of carbon dioxide via carbon dioxide product line 210. The filtered product then flows via water filter product line 211 into dryer 212 and water is removed via water product line 213. The resulting product is preferably a reduced content of non-digested material, suitable for recycling into the digester. The dried product flows through dryer product line 214 to treatment in a compressor, not shown. A liquid product from the digester tank 116 flows through liquid product line 127. A portion of this liquid product is recycled via recycle line 128, which splits into lower recycle feed line 129 and upper recycle feed line 130. The remaining, non-recycled liquid product flows through liquid product line 215 into separator 216. Recovered solids are removed through solids product line 217. The liquid product then flows through separator product line 218 into a low temperature reactor 219. From this reactor, liquid fertilizer is recovered via liquid fertilizer product line 220 and heat is recovered via heat product line 221. Remaining liquid is sent through system recycle line 223 into product storage tank 132. As in the previous example, there is an overflow line 133 handling overflow from the digester tank 116. There is also recycling of liquid via line 224 into digester tank 116. An equivalent line could have been present in the system depicted in FIG. 1. System recycling via line 134 is possible and a separate product cut can be pulled from storage tank 132 by means not depicted in the figure. The sloped bottom 136, which assists in channeling flow into line 127, is additionally noted.

Figure 3:
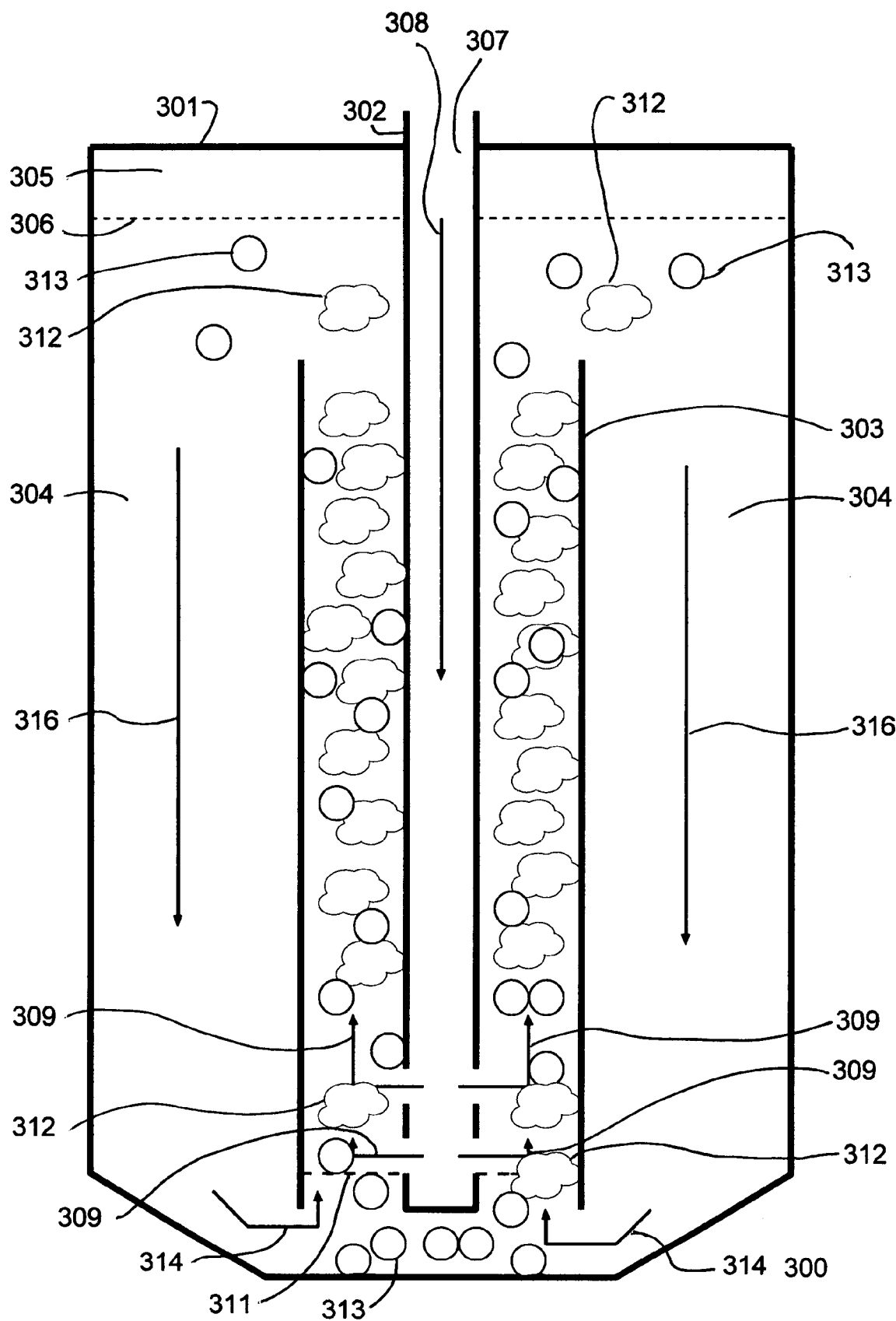
FIG. 3 depicts flow patterns of material in an anaerobic digester tank useful in the present invention.

Referring to FIG. 3, there is depicted the internal flow patterns possible within a digester tank system 300 in the practice of the present invention. The depiction drawn does not show product take-off or recycle lines, or other features, except that needed to understand the particular mixing feature addressed in this figure. There is depicted a cross-sectional view of digester tank 301. Tube 302 is shown concentrically aligned inside tube 303. The suspension elements of tube 303 within digester tank 301 are not shown but are understood by those in the art. Slurry mass 304 is provided in the tank 301. The system also has gaseous headspace 305 inside the digester tank 301 and above slurry mass 304. Interface surface 306 provides a boundary between slurry mass 304 and the gaseous headspace 305. During the operation of the digester system 300, there is a potential for undesired crust to form on interface surface 306. Recycled product gas 307 is provided into tube 302 and flows as indicated by the directional arrow of gas flow 308. Gas 307 flows in a downward direction and exits tube 302 through holes and flows along the directional arrow of gas flow 309. The product gas 307 flows up the annular space between tube 302 and tube 303 and exits into slurry mass 304. As gas 307 flows along gas flow 309, slurry mass 304 is drawn along path 314 and entrainment of slurry mass 304 occurs at about interface 311, pulling up with gas 307 also entrainment slurry mass 312 and solid mass 313. As gas 307, entrainment slurry mass 312 and solid mass 313 exit tube 303 into slurry mass 304, separation of materials occurs. Substantially all, if not all, of gas 307 flows upward and admixes with the contents of gaseous headspace 305 and slurry mass 312 and solid mass 313 mixes with slurry mass 304. This activity aids to prevent crust formation. As a result of slurry mass 304 entrainment at the bottom of tube 303 and the introduction of slurry mass 312 and solid mass 313 at the top of slurry mass 304, slurry mass 304 has downward slurry flow 316.

Figure 4:
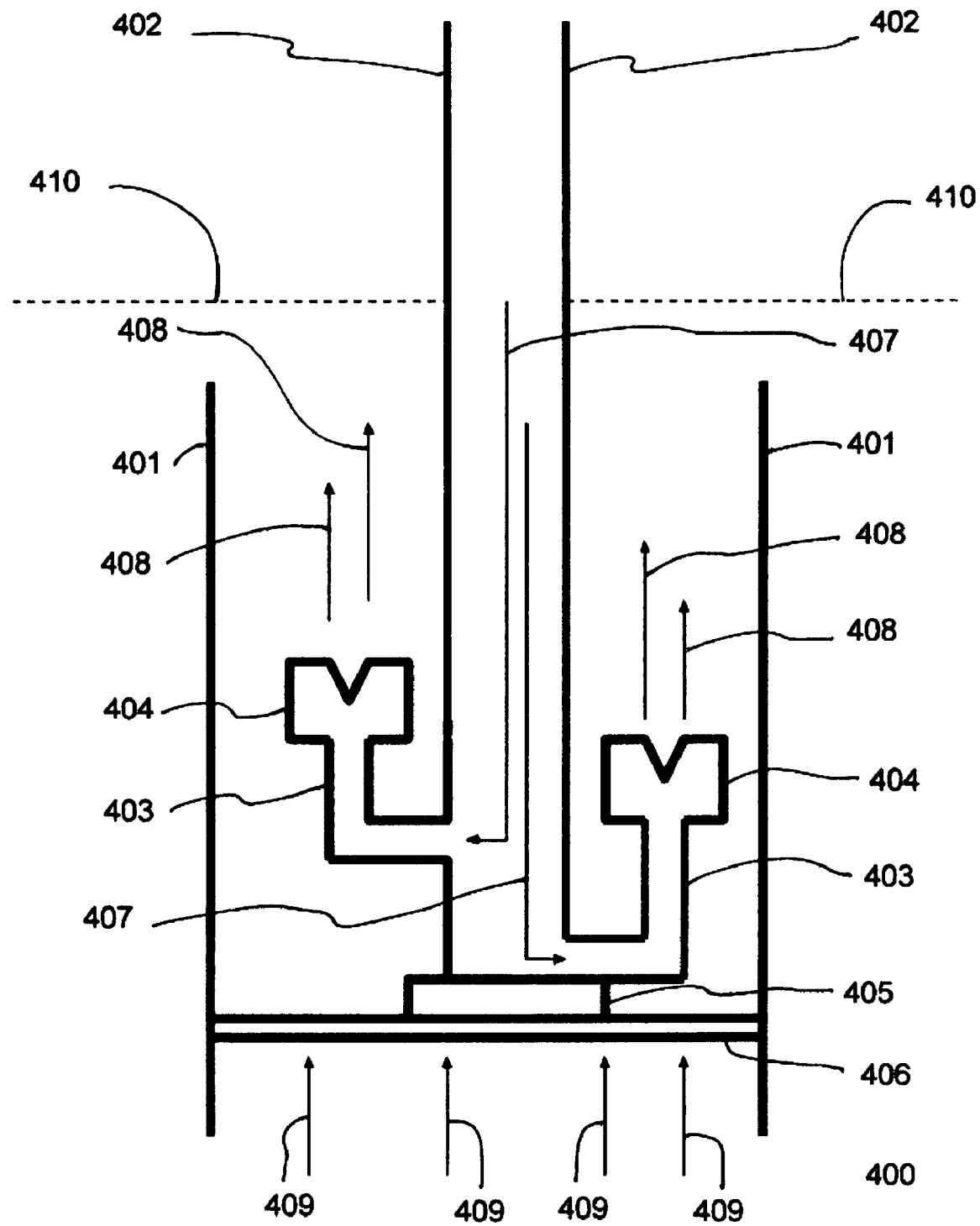
FIG. 4 depicts a nozzle system useful in the present invention.

Referring now to FIG. 4, there is depicted a nozzle system 400 for feeding material into a digester tank consistent with the present invention and useable in other applications as well. Similar to the systems discussed above, there is depicted a concentric tubes system composed of tube 401 and tube 402 positionable in a digester. Recycled gas flows along gas flow 407 into line 403 and exits through valve 404 into directioned upward flow 408. The valve 404 is a representation of an opened "duck-bill" valve or similar valve device. Valve 404 is manufactured of material which flexes into the "V" shaped opening shown at the top of valve 404. This opening is forced by the pressure force of gas flow 407. Tube 402 rested upon or joined to pad 405, which is braced by structure 406. Structure 406 may be a structure such as a grate, strut or cross bar, but must not be wide enough to block the entrained flow of material along path 409 from below. The external slurry top level is depicted by line 410.

Figure 5:
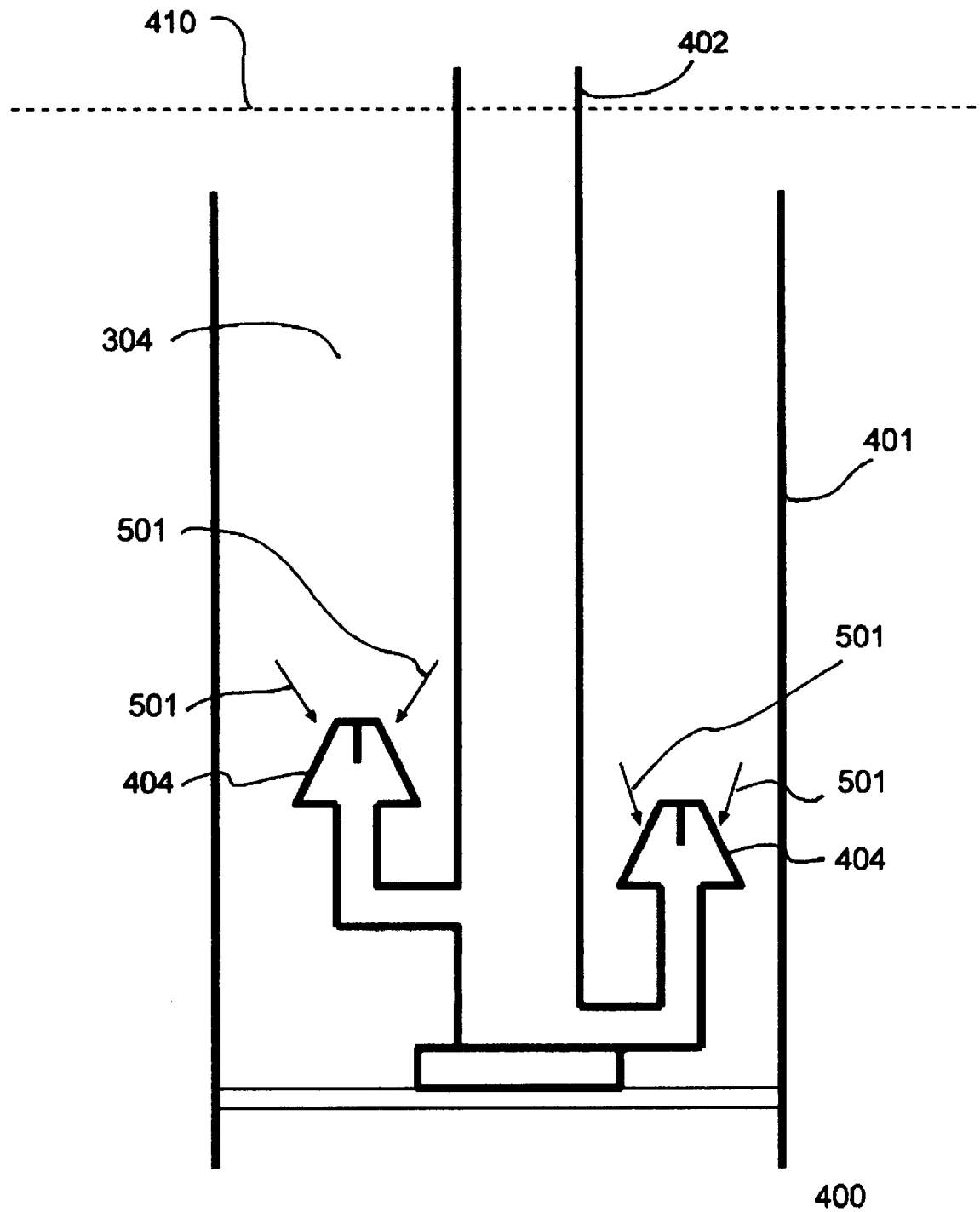
FIG. 5 depicts a nozzle system useful in the present invention.

Referring to FIG. 5, there is depicted the same system in FIG. 4, except that there is no gas flow 407 through tube 402. The slurry mass 304 has no flow in tube 401. This is because the fluid back pressure of slurry inside tube 401 has created pressure forces, depicted by arrow 501, onto valve 404, resulting in a closure of the valve. This is depicted by the absence of the open "V" shape in the valve shape.

In a preferred embodiment, the floor of the digester tank is sloped conically toward the center of the tank to facilitate take-up of the solid material.

Another embodiment of the present invention is a process for treating manure using anaerobic digestion to produce methane gas and recover nitrogen based products, such as liquid fertilizer and solid nitrogen compounds, and other products. The process comprises the steps of producing a manure having a reduced cellulose content and introducing the manure into a mixing vessel containing a digester liquid which comprises a thermophilic methanogen suitable for the production of methane from said manure.

The resulting admixture is maintained at a temperature effective to produce methane gas in the admixture. The temperature preferably is also effective to kill any pathogen which might be present in the admixture. The heating is at a temperature range and for an effective amount of time to break chemical bonds, producing methane, and destroy active bacteria present in the resultant liquid. The preferred range is that stated hereinabove.

Additionally, the pH of the admixture is maintained at an effective pH for the production of methane gas in the admixture. The admixture of manure and digester liquid in the mixing vessel is effectively well-mixed for an effective amount of time to produce a pumpable slurry. This liquid product is withdrawn from the mixing vessel and filtered to remove substantially all water insoluble solids therefrom and provide a resultant liquid containing ammonia and organic materials. Subsequently the ammonia is removed to produce a substantially ammonia-free liquid which can be recycled into the mixing tank upstream. Recycling can also be performed by withdrawing an effective amount of the digester liquid from the digester and recycling the withdrawn digester liquid to the mixing vessel for mixing with manure. Another recycle stream is attained by withdrawing an effective amount of the methane gas from the digester and recycling the withdrawn methane gas to the digester. The recycled gas stream to the digester can be done to provide mixing as disclosed hereinabove.

Another step performable is the filtering of the liquidous product, pumpable slurry to remove substantially all water insoluble solids therefrom. These water insoluble solids are collected and can be converted to an animal feed, a feed stock for production of chemicals, and a fuel source to satisfy energy and process heat requirements.

Accordingly, one embodiment of the present invention is a method for treating poultry manure using anaerobic digestion to produce a methane gas, comprising the steps of:

(a) forming an admixture having a solids content, said admixture comprising a poultry manure and a digester liquid which comprises a thermophilic methanogen suitable for the production of said methane gas from said poultry manure;

(c) controlling said poultry manure to have a composition of less than 5% by weight cellulose material;

(d) controlling said admixture at a thermophilic temperature range effective to kill a pathogen which might be present in the admixture, said temperature effective to produce methane gas in the admixture;

(d) controlling the pH of said admixture at a pH effective to product a methane gas in the admixture;

(e) controlling said solids content at a concentration effective to enable production of methane gas in said admixture;

(f) agitating said admixture, said agitating being effective to enable effective sensing of said temperature, said pH and said solids content of said admixture;

wherein said controlling of temperature, pH and solids content are effectively coordinated to control the production of methane gas and one or more nitrogen compositions in said admixture.

The preferred amount of agitation in step (f) is that which is also effective to return settled solids into a state of suspension in the digester.

Preferably, agitation is effective to entrain any settled solids in said admixture, to reduce or prevent the formation of crust on the surface of said admixture, and to create an effective degree of homogeneity in said admixture. This can be conveniently achieved by use of the apparatus described hereinabove.

The method is practiced so as to effectively control the nitrogen content of the digester to compose less than 2% by weight of the admixture.

As discussed hereinabove, the preferred thermophilic methanogen is selected from the group consisting of the genus *Methanosarcina* and the genus *Methanosaeta*. Preferably the temperature range is controlled to be from about 120 degrees to about 150 degrees and the pH ranges from 7 to about 7.5.

Preferably, as similarly discussed hereinabove, the present invention enables the operation of the digestion of poultry waste to be performed with a greater degree of control than previously done. For instance, the parameters of biological species, solid contents, temperature, pH produced methane gas products and produced nitrogen products are sensed so as to enable implementation control strategies for optimization of the system in accordance with the desired outcomes. Additionally, the flow velocities, pump speeds, fluid levels and pressures are also sensed. Interactive control of all of these parameters can be maintained via appropriate programmable controllers, process logic control computers and software systems, mainframe and otherwise. Feedback and feed forward schemes are possible and the additional parameters of forecasted economic value of reactants and products can be utilized in setting the control set points to achieve the near and long term desired outcomes in consumption of reactants and energy and in the quantity and quality of products and energy.

Other preferred embodiments incorporate the use of computer controls, the logic of such controls being utilized to attain a well-mixed slurry while maintaining effective solids loading. Such can include schemes which operate the fgas flows for mixing in either a continuous or an intermittent sequencing. Additionally, such enables differential mixing flows and variable reactants feeding rates to optimize biogas production.

A particular advantage of the present invention is the control of the pH of the digester. The well-mixing scheme allows accurate sampling and measurement of digester pH. This enables computer controls of feed rates, solid/liquid ratios and make-up water flows. The resulting preferred pH ranges from about 6.8 to about 7.4, more preferably 7.0 to about 7.2.

While the present invention has been described with regard to its critical components, it will be understood by those skilled in the art that various changes in detail may be made without departing from the spirit and scope of the invention.

What is claimed is:

1. A composition comprising a poultry litter derivative, one or more members of a thermophilic methanogenic genera, each of said member capable of growing by acetoclastic reaction, and water, wherein the said poultry litter derivative contains less than about 5 weight percent cellulosic material, said one or more members of a thermophilic methanogenic genera, and water are in an effective ratio to produce methane.

2. The composition of claim 1 wherein said poultry litter derivative is derived from broiler chickens litter.

3. The composition of claim 2 wherein said one or more members of a thermophilic methanogenic genera is selected from the group consisting of the genus *Methanosarcina* and the genus *Methanosaeta*.

4. The composition of claim 3 wherein said member is a *Methanosarcina barkeri*.

5. The composition of claim 4 wherein said member is *Methanosarcina barkeri* fusaro.

6. The composition of claim 3, wherein said pH is between 7.0 and about 7.5.

7. The composition of claim 2, wherein the pH of said composition is at least about 7.0 and no more than the maximum pH effective to produce methane from said composition.

8. The composition of claim 7, wherein said pH is between 7.0 and about 7.5.

9. The composition of claim 1, wherein the pH of the composition is at least about 7.0 and no more than the maximum pH effective to produce methane from said composition.

10. The composition of claim 1 wherein the temperature of the composition is ranges from about 120 degrees to no more than the maximum temperature effective to produce methane from said composition.

11. The composition of claim 10 wherein the temperature of the composition is between about 120 degrees and about 150 degrees.

12. The composition of claim 11 wherein said temperature is about 135 degrees.

13. An apparatus comprising
   a) a vessel suitable for containing an anaerobic digestion material, said anaerobic digestion material comprising animal waste and a biological agent suitable for converting said animal waste into a gaseous product and a liquidous product;
   b) a mixing means positioned with said vessel for mixing said anaerobic digestion materials, said mixing means comprising a first fluid injection means for injecting a first fluid imparting annular flow momentum in said anaerobic digestion materials in said vessel and a second fluid injection means for injecting a second fluid imparting axial flow momentum in said materials in said vessel;
   c) a temperature control means for controlling the temperature of said materials in said vessel;
   d) at least one feed line suitable for feeding said animal waste into said vessel;
   e) at least one gaseous product line for extracting a gaseous product from said vessel; and
   f) at least one liquidous product line for extracting a liquid product from said vessel, said vessel having a sloped bottom suitable for guiding said liquid product into said liquidous product line.

14. The apparatus of claim 13 wherein the said first fluid is a portion of said extracted gaseous product from said vessel and said second fluid is a portion of said extracted liquid product from said vessel.

15. The apparatus of claim 14 wherein said means for creating annular flow is at least one liquidous product recycle line dispensing angularly into said vessel.

16. The apparatus of claim 13 wherein said means for creating annular flow is at least one feed line dispensing directionally into said vessel.

17. The apparatus of claim 13 wherein said sloped bottom being coated with an epoxy to reduce or prevent adherence of material to said sloped bottom.

18. The apparatus of claim 13 wherein said first injection means comprises a first tube vertically suspended by fastening means within said vessel and a second tube vertically concentrically configured inside said first tube, said first and second tubes having a vertical axis at or near the vertical axis of said vessel, said first tube having a top opening positioned below the upper surface of said anaerobic digestion material within said vessel and having a bottom opening positioned within said vessel to open within the portion of said vessel containing said liquidous product, said second tube being a recycle line containing at least a portion of said gaseous product and terminating inside said first tube in proximity to said bottom opening of said first tube, wherein said second tube comprises one or more outlets for said recycled gaseous product effectively shaped and configured so as to entrain said liquidous product from said vessel into said bottom opening of said first tube and carry said entrained liquidous product for delivery below the upper surface of said anaerobic digestion material.

19. The apparatus of claim 18 wherein the bottom opening of said first tube is in sufficient proximity to the bottom of said vessel so as to entrain at least a portion of any settled solid material on or near said sloped bottom of said vessel.

20. A method for treating poultry manure using anaerobic digestion to produce a methane gas, comprising the steps of:
   (a) forming an admixture having a solids content, said admixture comprising a poultry manure and a digester liquid which comprises a thermophilic methanogen suitable for the production of said methane gas from said poultry manure;
   (b) controlling said poultry manure to have a composition of less than 5% by weight cellulose material;
   (c) controlling said admixture at a thermophilic temperature range effective to kill a pathogen which might be present in the admixture, said temperature effective to produce methane gas in the admixture;
   (d) controlling the pH of said admixture at a pH effective to product a methane gas in the admixture;
   (e) controlling said solids content at a concentration effective to enable production of methane gas in said admixture; and
   (f) agitating said admixture, said agitating being effective to enable effective sensing of said temperature, said pH and said solids content of said admixture;
   wherein said controlling of temperature, pH and solids content are effectively coordinated to control the production of methane gas and one or more nitrogen compositions in said admixture.

21. The method of claim 20 wherein said agitating is effective to entrain any settled solids in said admixture, to reduce or prevent the formation of crust on the surface of said admixture, and to create an effective degree of homogeneity in said admixture.

22. The method of claim 20 wherein said controlling of temperature, pH and solids content are effectively coordinated to control the production of methane gas and one or more nitrogen compositions in said admixture such that said one or more nitrogen compositions are effectively controlled to compose less than 2% by weight of the admixture.

23. The method of claim 20 wherein said thermophilic methanogen is selected from the group consisting of the genus *Methanosarcina* and the genus *Methanosaeta*.

24. The method of claim 20 wherein said temperature range is from about 120 degrees to about 150 degrees.

25. The method of claim 20 wherein said pH ranges from 7 to about 7.5.

* * * * *